United States Patent [19]

Jones

[11] 3,947,427
[45] Mar. 30, 1976

[54] 2-(ISOTHIOCYANATOMETHYL)-1,3-BUTADIENE AND POLYMERS THEREOF
[75] Inventor: Giffin D. Jones, Midland, Mich.
[73] Assignee: The Dow Chemical Company, Midland, Mich.
[22] Filed: Dec. 16, 1974
[21] Appl. No.: 533,104

Related U.S. Application Data
[62] Division of Ser. No. 303,647, Nov. 3, 1972, abandoned.

[52] U.S. Cl.................... 260/77.5 R; 260/453 AL
[51] Int. Cl.² ....................................... C08G 18/02
[58] Field of Search ............................. 260/77.5 R

[56] References Cited
UNITED STATES PATENTS
3,654,336   4/1972   Krimm et al. ............... 260/77.5 R Primary Examiner—M. J. Welsh
Attorney, Agent, or Firm—L. Wayne White

[57] ABSTRACT 2-(Isothiocyanatomethyl)-1,3-butadiene is a novel compound which is represented by the formula

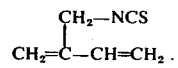

It can be homopolymerized or interpolymerized with other vinyl monomers to form many useful addition polymers.

3 Claims, No Drawings

2-(ISOTHIOCYANATOMETHYL)-1,3-BUTADIENE AND POLYMERS THEREOF

This is a division of application Ser. No. 303,647 filed Nov. 3, 1972 now abandoned.

SUMMARY OF THE INVENTION

I have discovered the compound 2-(isothiocyanatomethyl)-1,3-butadiene and vinyl addition polymers thereof.

The novel compound is represented by the formula

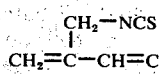
$$CH_2=C-CH=CH_2 . \qquad I$$

It is a water-insoluble liquid which has a density of 1.0174 and a refractive index of 1.5660 at 25°C. It is conveniently prepared by contacting 2-chloromethylbutadiene with ammonium thiocyanate in t-butanol at a temperature of from about 50° to about 80°C until the product is formed and thereafter recovering the product by distillation (b.p. 55°C at 4 mm Hg).

The novel compound is a difunctional monomer which can be homopolymerized or interpolymerized with other ethylenically unsaturated monomers to form new and useful vinyl addition polymers. Such polymers contain at least 0.5 mole percent of I in interpolymerized form as a unit of the formula

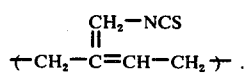

The polymers are prepared via conventional techniques as shown, for example, in "Polymer Processes" by C. E. Schildknecht, Interscience Publishers, Inc., N.Y. (1956), Volume X of the "High Polymers" series; the disclosure of which is herein incorporated by reference.

The novel polymers can be cured by reaction with a polyfunctional curing agent(s) bearing a plurality of groups which are reactive with the pendant isothiocyanato groups on the polymer. Suitable such compounds include polyols (such as ethylene glycol, polyethylene glycol, bisphenol A, etc.), polyamines (such as ethylene diamine, diethylenetriamine, polyethylenimine, etc.) and other such polyfunctional materials. When the reactant is a glycol a catalyst is required. Preferable catalysts are a tertiary amine or a tin compound such as stannous octoate.

Alternatively, the polymers of I can be used as cross-linking agents for polymers bearing groups reactive with the isothiocyano group. E.g., polymers of I can be used to cross-link an acrylamide copolymer containing an amino group (primary or secondary), a hydroxyl or a free carboxyl. Reaction with a carboxyl requires heating, preferably to 150°C or higher. E.g. copolymers of acrylamide with hydroxyethylacrylate, amino-ethylmethacrylate or vinylbenzylamine can be cross-linked using polymers of I.

The addition polymers of I vary in length from oligomers on up to high molecular weight polymers having a molecular weight of several thousand or more. It is well known to those skilled in the art how to obtain vinyl addition polymers within a particular molecular weight range; e.g. by choice of reaction temperature, time, concentration and type of initiator, etc.

Vinyl monomers which are polymerizable in such addition polymerization reactions form a known class of compounds. Any monomer from this known group may be interpolymerized with I to form a useful polymer which can be formed into a useful article.

Suitable such vinyl monomers include vinyl aromatic monomers (e.g. styrene, α-methylstyrene, vinyl-toluene, ar-t-butylstyrene, ar-chlorostyrene, ar,ar-dichlorostyrene, ar-bromostyrene, vinylnaphthalene, and the like); conjugated diolefins (e.g. butadiene, 2-chloro-methylbutadiene, chloroprene, isoprene, 2,3-dimethyl-1,3-butadiene, and the like); alkyl, hydroxyalkyl and protonated amino-alkyl esters of α,β-ethylenically unsaturated carboxylic acids (e.g. the methyl, ethyl, propyl, butyl, hydroxyethyl, 2-hydroxypropyl, 2-hydroxybutyl, 2-aminoethyl and 2-aminopropyl acrylates, methacrylates, maleates, itaconates and fumarates, and the like); α,β-ethylenically unsaturated carboxamides (e.g. acrylamide, N-methylolacrylamide, methacrylamide, and the like); α,β-ethylenically unsaturated nitriles (e.g. acrylonitrile, methacrylonitrile, fumaronitrile, and the like); and other such vinyl monomers. Preferred vinyl monomers are of course styrene, butadiene, isoprene, lower alkyl (1–4 carbon atoms) acrylates and methacrylates, and acrylonitrile, based on current commercial availability and economics.

The following examples further illustrate the invention.

PREPARATION OF (I)

Equimolar amounts of 2-chloromethyl-1,3-butadiene and ammonium thiocyanate were dissolved in t-butanol and warmed at 50°–60°C for approximately 5 hours with continuous stirring and in the presence of 100 ppm catechol (a polymerization inhibitor). Vapor phase chromatography (vpc) analysis of the mixture indicated at least 85% conversion of reactants. The reaction produced I and its thermodynamically less stable isomer 2-(thiocyanatomethyl)-1,3-butadiene which rearranged to I upon distillation at 7 mm pressure or higher. The desired product, I, was recovered by distillation under vacuum (head temperature 65°C at 7 mm Hg) at a 5:1 reflux ratio using an 18 inch Oldershaw column. Elemental analysis for $C_6H_7NS$ showed 11.22% N and 25.09% S (theoretical is 11.19% N and 25.61% S). The structure of the product was further confirmed by infrared and nuclear magnetic resonance spectra.

VINYL ADDITION POLYMERS OF (I)

I was homopolymerized by contacting a solution of I in t-butanol with a catalytic amount of azo-bis-isobutyronitrile (AIBN) for 5 hours. The solvent and other volatiles were removed under vacuum leaving a solid, chloroform-soluble homopolymer of I. The homopolymer was highly effective in removing mercury ions from aqueous solution by merely contacting the homopolymer with the mercury polluted solution for a few hours. The thiourea and thiocarbazide derivatives of said homopolymer were prepared by contacting the polymer with ammonia and hydrazine vapors, respectively. These derivatives were likewise useful in chelating mercury ions.

In like manner, a water-soluble tan solid interpolymer was prepared by contacting for 5 hours 1 mole of I and 0.7 mole of ar-vinylbenzyltrimethyl ammonium chloride dissolved in t-butanol with a catalytic amount of AIBN. The polymer was essentially equimolar in each monomer. Aqueous solutions of this interpolymer were blended with aqueous solution of partially hydrolyzed polyacrylamide or poly(2-(2-hydroxyethylaminomethyl)-1,3-butadiene). A clear stiff gell formed rapidly in each instance. The interpolymer is thus useful as a cross-linking agent for polymers bearing reactive hydroxyl, amino and/or coacervating groups (e.g. carboxyl groups).

A water-soluble interpolymer having similar reactivity was obtained when a mixture of acrylamide (10 g.) and I (0.95 g.) dissolved in t-butanol (90 g.) was warmed for 4 hours at 60°C in the presence of o-dichlorobenzene (0.05 g.) and AIBN (0.04 g.). The o-dichlorobenzene was added as an internal standard for vpc analysis of the product.

Other vinyl addition interpolymers of I can be similarly prepared by using the above illustrated solution technique or by using emulsion polymerization techniques. Emulsion polymerization techniques are particularly suitable when the comonomer is a water-insoluble vinyl monomer (such as styrene, butadiene, isoprene, etc.).

I claim:

1. A vinyl addition polymer comprising in interpolymerized form at least 0.5 mole percent of 2-(isothiocyanatomethyl)-1,3-butadiene as a unit of the formula

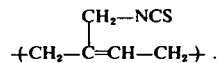

2. The polymer defined by claim 1 wherein said polymer is an interpolymer of
    A. 2-(isothiocyanatomethyl)-1,3-butadiene, and
    B. a monomer selected from the group consisting of: vinyl aromatic monomers; conjugated diolefins; alkyl-, hydroxyalkyl-, and protonated aminoalkyl esters of α,β-ethylenically unsaturated carboxylic acids; α,β-ethylenically unsaturated carboxamides; and α,β-ethylenically unsaturated nitriles.

3. The polymer defined by claim 2 wherein (B) is styrene, butadiene, isoprene, a lower alkyl acrylate or methacrylate, or acrylonitrile.

* * * * *